(12) United States Patent
Vetter et al.

(10) Patent No.: US 6,491,665 B1
(45) Date of Patent: *Dec. 10, 2002

(54) MEDICAL SYRINGE

(75) Inventors: Udo J. Vetter, Ravensburg; Thomas Otto, Weingarten; Petra Hund, Berg, all of (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/516,651

(22) Filed: Mar. 1, 2000

(30) Foreign Application Priority Data

Mar. 5, 1999 (DE) .......................................... 199 09 824

(51) Int. Cl.⁷ ................................................ A61M 5/00
(52) U.S. Cl. ........................................ 604/181; 604/187
(58) Field of Search ................................ 604/181, 187, 604/905; 215/DIG. 3

(56) References Cited

U.S. PATENT DOCUMENTS 5,785,691 A   7/1998  Vetter .......................... 604/187

*Primary Examiner*—Teresa Walberg
*Assistant Examiner*—Leonid M Fastovsky
(74) *Attorney, Agent, or Firm*—Herbert Dubno; Andrew Wilford

(57) ABSTRACT

A syringe assembly has a syringe body adapted to be filled with an injectable liquid and having an annular neck defining an axis and having an axially outwardly open outlet. The neck is adapted to carry a needle. An elastomeric plug engaged axially inward with the neck closes the outlet and a holding ring is fixed to the neck below the plug. A retaining sleeve around the neck is fixed to the holding ring and a cup-shaped safety cap is fixed to the plug and has an end edge confronting the retaining sleeve and spaced axially therefrom. Frangible formations extend from the cap edge to the sleeve.

15 Claims, 5 Drawing Sheets

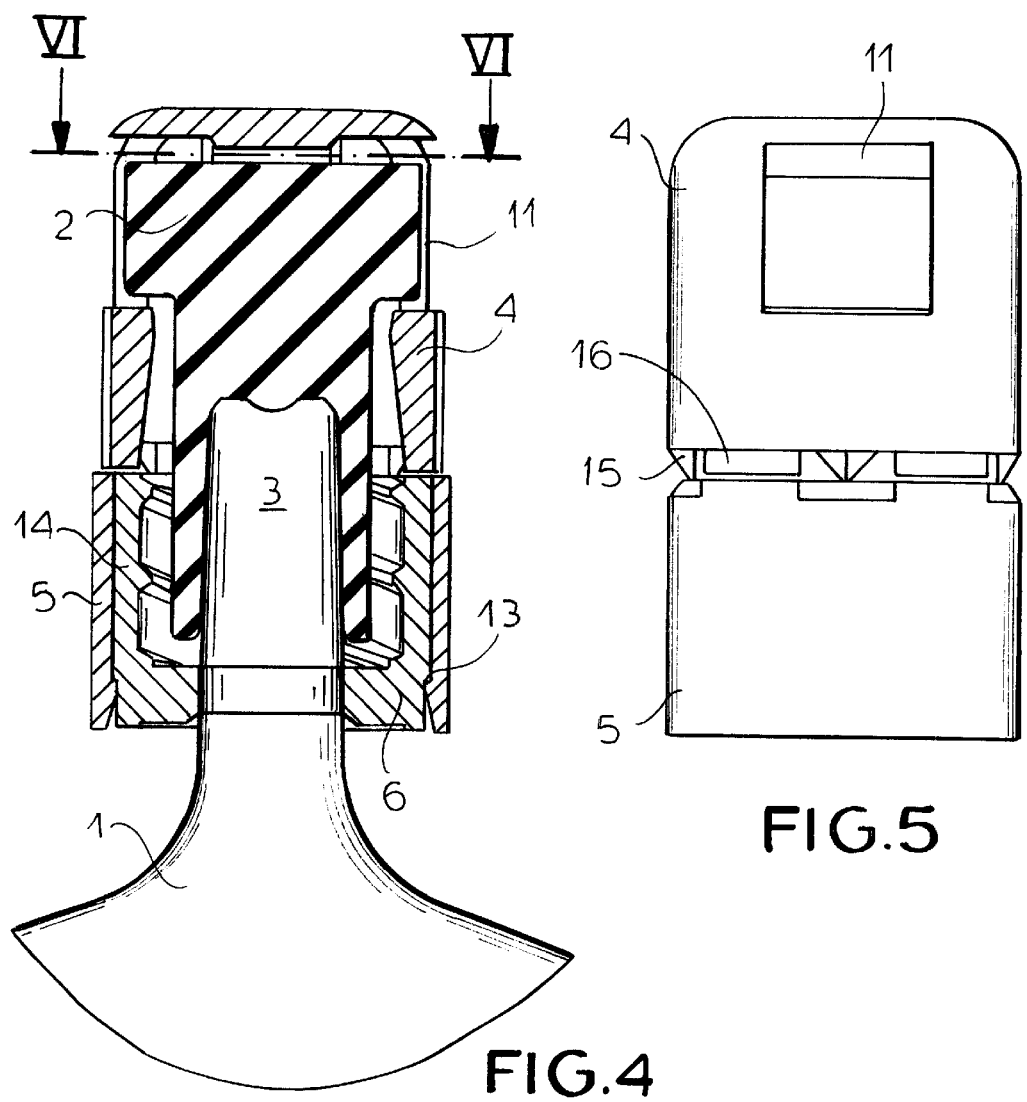
FIG.4
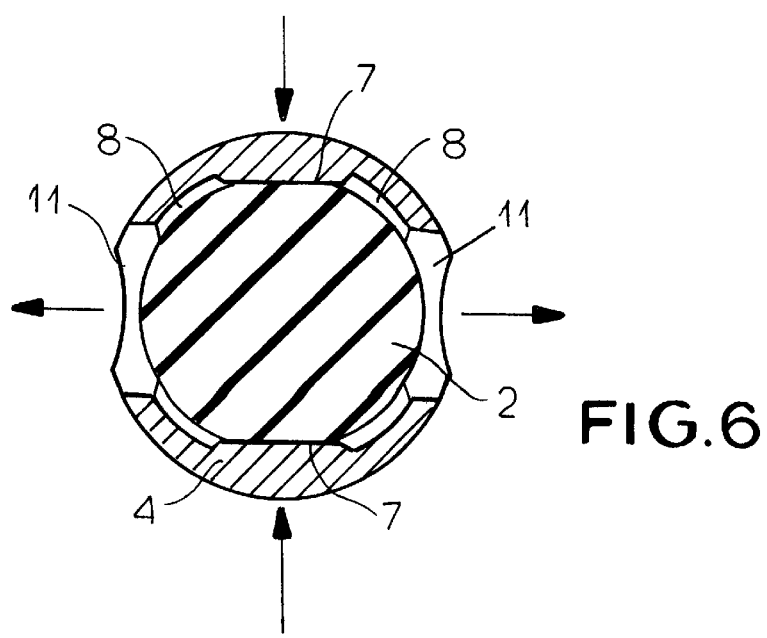
FIG.5
FIG.6

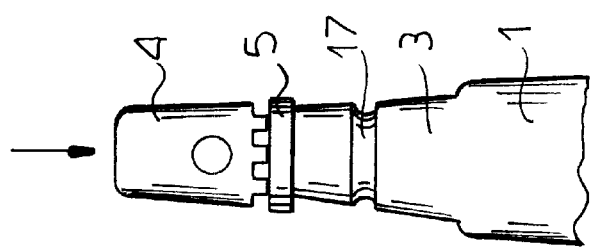
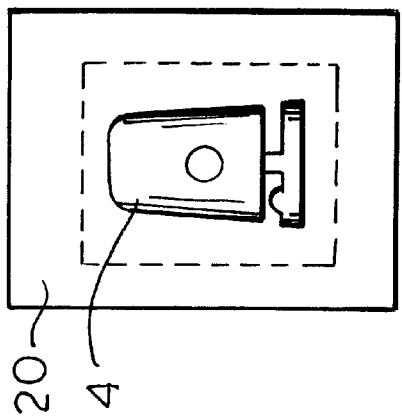
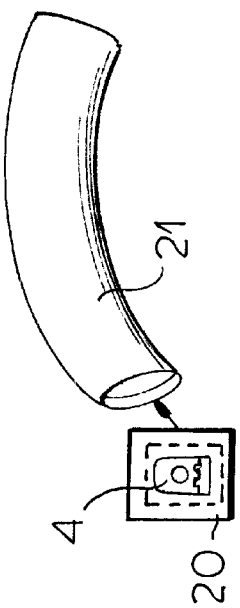
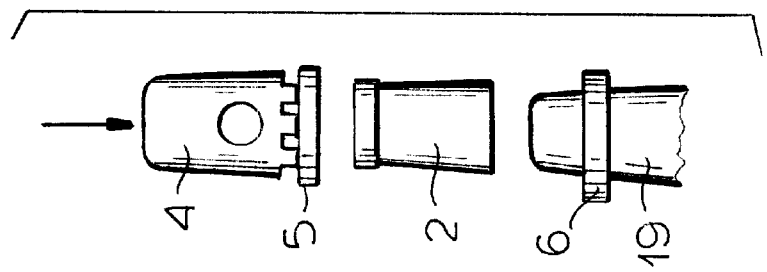

MEDICAL SYRINGE

FIELD OF THE INVENTION

The present invention relates to a medical syringe. More particularly this invention concerns a prefilled syringe body ready for installation of a needle and use, and to a method of assembling such a syringe.

BACKGROUND OF THE INVENTION

A syringe assembly has as described in commonly owned U.S. Pat. No. 5,785,691 a syringe body adapted to be filled with an injectable liquid and having an annular neck defining an axis and forming an axially outwardly open outlet adapted to hold a needle insert that blocks the outlet. The insert is formed with an axially through going passage so that a needle can be inserted axially through the passage of the insert into the body. A retaining collar engaged around the neck holds the insert in the outlet and a plug engaged in the passage fits over the retaining collar. A retaining sleeve fixed around the collar at the neck holds the collar on the neck and has an annular and axially outwardly directed end edge. A cup-shaped safety cap bearing axially inward on the plug has an annular and axially inwardly directed end edge confronting the retaining-sleeve edge and spaced axially therefrom by a gap which is bridged by a plurality of angularly spaced frangible webs unitarily formed with the sleeve and with the cap and extending from the cap edge to the sleeve edge.

The individual parts forming the cap subassembly, that is the insert and the cap, are made on different machines and must be mounted seriatim on the syringe body. Since this final assembly must be done after the syringe body is sterilized and filled, the parts forming the cap subassembly must also be sterile. Since these parts are made by different machines and at different locations, this entails a multipart sterilizing operation in the final clean room where the syringes are capped and prepared for transit.

OBJECTS OF THE INVENTION

It is therefore an object of the present invention to provide an improved syringe assembly.

Another object is the provision of such an improved syringe assembly which overcomes the above-given disadvantages, that is which is easier to assemble with the syringe body under sterile conditions.

A further object is to provide an improved method of assemblying a syringe.

SUMMARY OF THE INVENTION

A syringe assembly has according to the invention a syringe body adapted to be filled with an injectable liquid and having an annular neck defining an axis and having an axially outwardly open outlet. The neck is adapted to carry a needle. An elastomeric plug engaged axially inward with the neck closes the outlet and a holding ring is fixed to the neck below the plug. A retaining sleeve around the neck is fixed to the holding ring and a cup-shaped safety cap is fixed to the plug and has an end edge confronting the retaining sleeve and spaced axially therefrom. Frangible formations extend from the cap edge to the sleeve.

With the system of this invention the individual parts of the cap subassembly can be manufacture and put together in advance. Thus at the final assembly stage the cap subassembly is put onto the normally prefilled syringe body in a single operation made possible by the use of the holding ring. While the cap is made of a relatively hard and brittle material and similarly the syringe body is made of glass or a hard plastic, the holding ring is somewhat softer so that, even though the plug and holding ring are in the hard cap, they can be fitted over the hard syringe body while assembled together. The saving on steps in assembly is substantial, since the entire cap subassembly can be sterilized at the same time.

The safety cap according to the invention is formed with a pair of radially inwardly projecting ribs engaging the plug. They hold the plug solidly in place while still leaving space for sterilizing liquid or gas to flow through the cap subassembly.

The safety cap itself is formed with an internal annular shoulder and the plug has an enlarged portion engaged over the shoulder to fix the plug permanently in the cap once it is pushed into place. In addition the safety cap is formed with at least one radially throughgoing aperture that gives the end user the ability to see if the plug is properly in place before cracking off the cap. The ribs are normally provided 90° offset from the windows so they cause the plug to bulge out the windows, further increasing the hold of the plug in the cap.

The retaining sleeve is formed with a radially inwardly open groove in which the holding ring is fitted. In another system the retaining sleeve is formed with an axially outwardly directed shoulder and the holding ring engages over the shoulder. In both situations the holding ring must be damaged or destroyed to separate it from the retaining sleeve once installed therein.

The holding ring itself according to the invention has an outwardly projecting and axially centered collar formed with an internal luer thread. Thus once the cap is broken off the retaining sleeve and removed along with the plug, a needle subassembly including an externally threaded luer-type base can be screwed right into the collar of the holding ring.

The retaining sleeve in accordance with the invention has a sleeve edge axially confronting and juxtaposed at a gap with the cap end edge. The formations include a plurality of frangible webs unitary with and extending axially between the edges. In addition a plurality of angularly spaced spacer blocks formed on one of the edges alternate with the webs and project at least partially across the gap toward the other edge. The webs are angularly equispaced about the axis and taper toward the retaining sleeve. Thus the axially inwardly effective force applied to the cap to force the holding ring over the neck will be transmitted by the blocks to the retaining sleeve while the frangible webs deform slightly elastically. The cap will not separate from the retaining sleeve unless it is tipped, twisted, or pulled axially out relative to it.

The neck is formed with an outwardly open seat receiving the holding ring. As a result the holding ring will be slightly elastically deformed as it is fitted over the neck, but the axial force to do this will be transmitted by the blocks from the cap to the sleeve carrying the holding ring. Any other force will cause the frangible webs to break well before the holding ring would pull of the neck, so the system is highly tamper proof. Any attempt to open and reclose the syringe would be evident.

The method according to the invention basically comprises the steps of supporting the holding ring on a support element, then fitting the plug over the support element adjacent the holding ring thereon and fitting the cap, formations, and sleeve over the holding ring and plug so that the plug seats and fixes itself in the cap and the holding ring seats and fixes itself in the sleeve. This action forms an integral assembly of the ring, plug, cap, formations, and sleeve which is then sterilized and fitted as one piece over the neck of the body until the ring locks in place thereon with the plug blocking the outlet. Of course according to the invention the ring, plug, cap, formations, and sleeve are fitted together under sterile conditions.

Once sterilized, the assembled ring, plug, cap, formations, and sleeve are encased in a hermetic envelope. This envelope is transported another clean room and there them to the syringe body. Production is therefore greatly rationalized and simplified with the sterile cap assemblies being produced in advance at another location and enclosed in respective hermetic envelopes. In another clean room at the fillers site the packages are opened and the sterile cap assemblies are fitted to the normally prefilled syringe bodies.

BRIEF DESCRIPTION OF THE DRAWINGS

The above and other objects, features, and advantages will become more readily apparent from the following description, reference being made to the accompanying drawing in which:

FIG. 4 is an axial section through another cap subassembly according to the invention;

FIG. 5 is a side view of the assembly of FIG. 4;

FIG. 6 is a section taken along line VI—VI of FIG. 4;

FIGS. 9a to 9d are schematic diagrams illustrating the method of this invention.

SPECIFIC DESCRIPTION

Figure 1A:
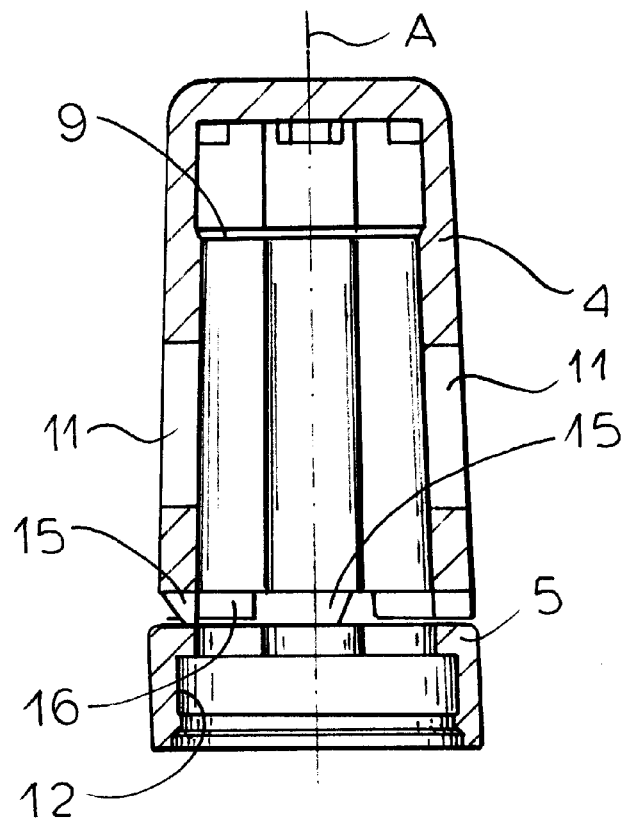
FIGS. 1a, 1b, and 1c are axial sections through the three parts of the cap subassembly of the syringe according to the invention.
Figure 1B:
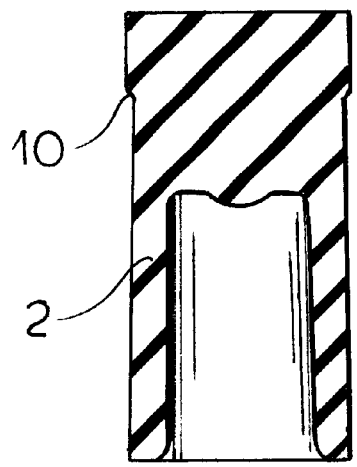
Figure 1C:
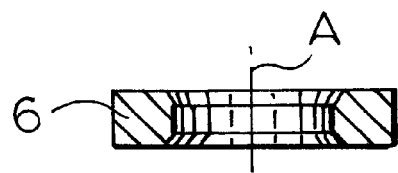
Figure 2:
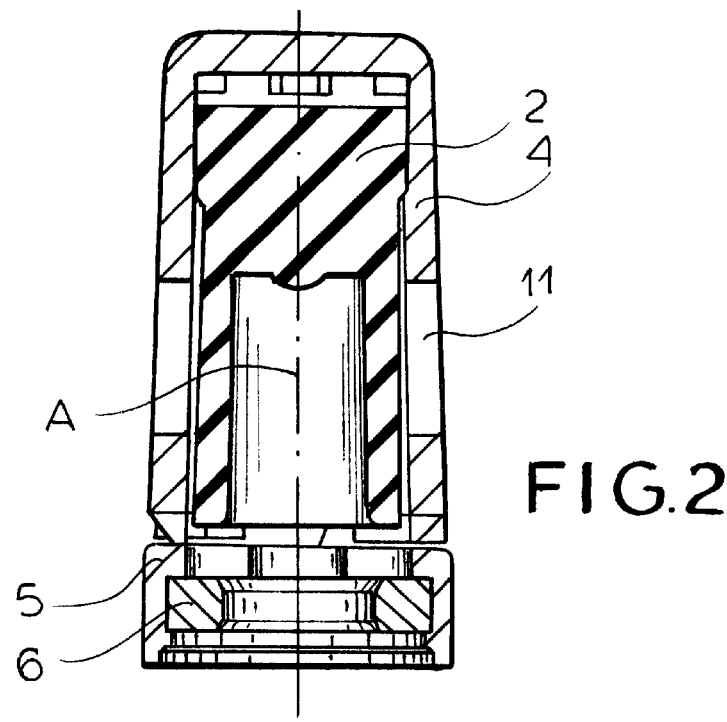
FIG. 2 is an axial section through the complete cap subassembly.
Figure 3:
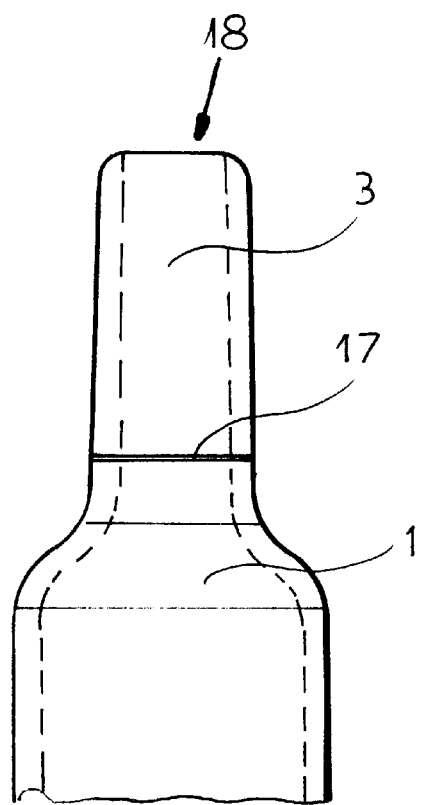
FIG. 3 is a side view of a syringe body usable with the cap subassembly.

As seen in FIGS. 1a, 1b, 1c, 2, and 3 a syringe body 1 is typically a glass or plastic cylinder with a small-diameter annular neck 3 formed as a Luer cone with an outlet 18 for receiving a collar carrying a needle. The body 1 can be prefilled with a medicament and prefitted with an unillustrated plunger so that, once equipped with a needle, it is ready to use. A plug or tip cap 6 which is basically shaped as a downwardly open cup of an elastomer is fitted over the neck 3 to keep it sterile and a safety cap 4 is secured in place over the plug 6 by means of a retaining sleeve 5 and holding ring or washer 6. The parts are all symmetrical to a central axis A.

The plug 6 is solidly mounted in the cap 4, to which end the cap 4 has an axially outwardly directed shoulder or undercut 9 that fits with an axially inwardly directed undercut or shoulder 10 of the plug 2. In addition the sides of the cap 4 are formed with throughgoing apertures 11 that allow sterilizing liquid or steam to get all through these parts and also allow the user to visually check that the plug 2 is in place.

The cap 4 is attached to the sleeve 5 by frangible webs 15 that taper toward the sleeve 5. In addition short spacer blocks 16 are formed on the lower edge of the cap 4 in close juxtaposition with the sleeve 5 so that any axial inward forces exerted on the cap 4 will not break the webs 15. Instead these forces will be transmitted after minor elastic deformation of the webs 15 to the upper edge of the sleeve 5 by the blocks 16.

The sleeve 5 has a radially inwardly open groove or seat 12 in which the retaining washer 6 fits. In turn the inner periphery of this washer 6 is inwardly convex and fits tightly in an outwardly open groove 17 formed in the neck 3.

Figure 7:
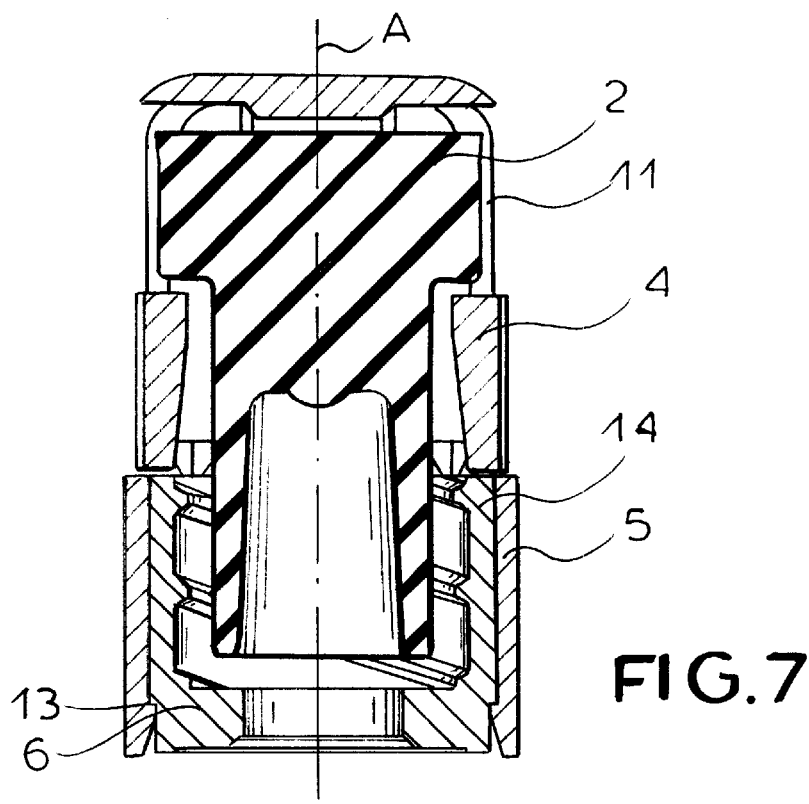
FIG. 7 is an axial section through the cap subassembly of FIG. 7.
Figure 8:
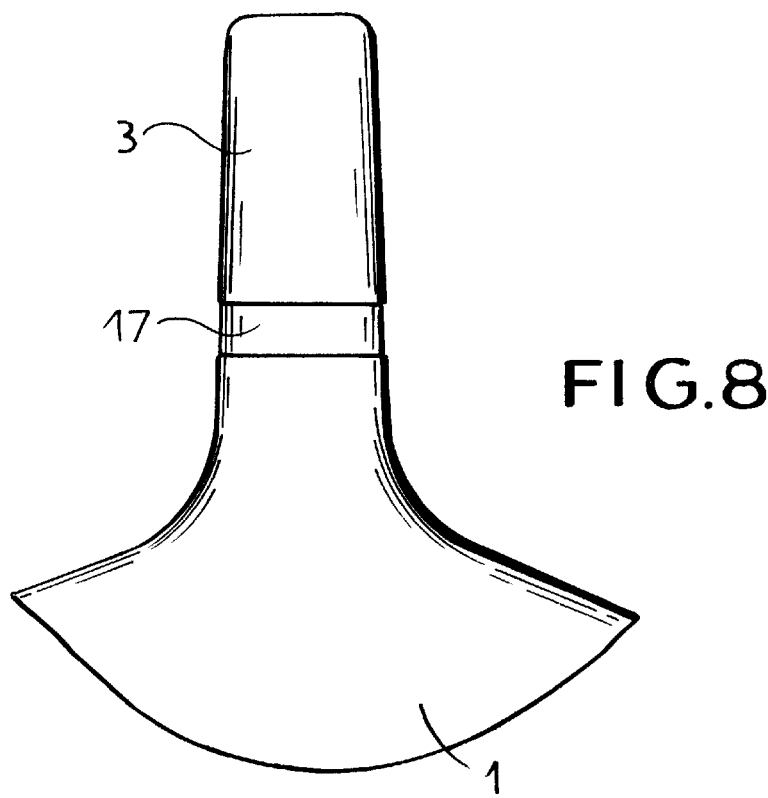
FIG. 8 is a side view of the syringe body used with the subassembly of FIG. 4.

In the arrangement of FIGS. 4 to 8 the ring or washer 6 is formed with an axially inwarldy directed shoulder 13 fitting with a complementary shoulder of the retaining sleeve 5. In addition it is formed with an axially outwardly directed tubular extension 14 internally formed with a luer-lock screwthread so that, once the top part inlcuding the cap 4 and plug 2 is broken off, a standard luer-lock needle can be fitted screwed to th4 collar 14 left on the neck 3. In this arrangement the cap 4 is formed 90° offset from the windows 11 with axially extending internal ribs 7 so that gaps 8 are left through which fluid can flow for sterilizing the cap subassembly. The head of the plug 2 is so large that it bulges out into the windows 11 to tightly lock the plug 2 in the cap 4.

According to the invention the cap subassembly is made as shown in FIG. 9a by fitting first the sleeve 5 and then the plug 2 to an upwardly pointing assembly cone 19. Then the cap 4 is pressed down to fix the plug 2 tightly in the cap 4 and simultaneously fix the washer 6 in the sleeve 5. This subassembly is then sterilized and sealed in a hermetic package, for instance the plastic bag 20 shown in FIG. 9b. The bagged subassembly is sent as indicated in FIG. 9c through a pneumatic transport system 21 from the clean room where the assembly and sterilizing of FIGS. 9a and 9b takes place to another clean room where as shown in FIG. 9d the cap subassembly is unbagged and fitted to a prefilled syringe body 3. Pressing the cap subassembly down on the syringe body 3 causes the washer 6 to fit tightly into the seat formation 17 and secure the parts together so tightly that it is impossible to separate them without damaging them or leaving obvious evidence of tampering.

We claim:

1. A syringe assembly comprising:
    a syringe body adapted to be filled with an injectable liquid and having an annular neck defining an axis and having an axially outwardly open outlet, the neck being adapted to carry a needle;
    an elastomeric plug engaged axially inward with the neck and closing the outlet;
    a holding ring fixed to the neck below the plug;
    a retaining sleeve around the neck fixed to the holding ring;
    a cup-shaped safety cap fixed to the plug and having an end edge confronting the retaining sleeve and spaced axially therefrom; and
    frangible formations extending from the cap edge to the sleeve.

2. The syringe assembly defined in claim 1 wherein the safety cap is formed with a pair of radially inwardly projecting ribs engaging the plug.

3. The syringe assembly defined in claim 1 wherein the safety cap is formed with an internal annular shoulder and the plug has an enlarged portion engaged over the shoulder.

4. The syringe assembly defined in claim 1 wherein the safety cap is formed with at least one radially throughgoing aperture.

5. The syringe assembly defined in claim 1 wherein the retaining sleeve is formed with a radially inwardly open groove in which the holding ring is fitted.

6. The syringe assembly defined in claim 1 wherein the retaining sleeve is formed with an axially outwardly directed shoulder and the holding ring engages over the shoulder.

7. The syringe assembly defined in claim 1 wherein the holding ring has an outwardly projecting and axially centered collar formed with an internal luer thread.

8. The syringe assembly defined in claim 1 wherein the retaining sleeve has a sleeve edge axially confronting and juxtaposed at a gap with the cap end edge, the formations including a plurality of frangible webs unitary with and extending axially between the edges, the assembly further comprising
   a plurality of angularly spaced spacer blocks formed on one of the edges, alternating with the webs, and projecting at least partially across the gap toward the other edge.

9. The syringe assembly defined in claim 8 wherein the webs are angularly equispaced about the axis.

10. The syringe assembly defined in claim 8 wherein the webs taper toward the retaining sleeve.

11. The syringe assembly defined in claim 1 wherein the neck is formed with an outwardly open seat receiving the holding ring.

12. A method of making a syringe assembly including
   a syringe body adapted to be filled with an injectable liquid and having an annular neck defining an axis and having an axially outwardly open outlet, the neck being adapted to carry a needle;
   an elastomeric plug engaged axially inward with the neck and closing the outlet;
   a holding ring on the neck below the plug;
   a retaining sleeve around the neck on the holding ring;
   a cup-shaped safety cap on the plug and having an end edge confronting the retaining sleeve and spaced axially therefrom,
frangible formations extending from and unitary with the cap edge to the sleeve, the method comprising the steps of:
   supporting the holding ring on a support element;
   fitting the plug over the support element adjacent the holding ring thereon;
   fitting the cap, formations, and sleeve over the holding ring and plug so that the plug seats and fixes itself in the cap and the holding ring seats and fixes itself in the sleeve so as to form an integral assembly of the ring, plug, cap, formations, and sleeve;
   sterilizing the assembly;
   fitting the assembly as one piece over the neck of the body until the ring locks in place thereon with the plug blocking the outlet.

13. The syringe assembly defined in claim 12 wherein the ring, plug, cap, formations, and sleeve are fitted together under sterile conditions.

14. The syringe assembly defined in claim 13 wherein after fitting together, the ring, plug, cap, formations, and sleeve are encased in a hermetic envelope.

15. The syringe assembly defined in claim 14, further comprising the step of
   transporting the hermetic envelope containing the ring, plug, cap, formations, and sleeve to another clean room and there fitting them to the syringe body.

* * * * *